United States Patent [19]
Ghim

[11] Patent Number: 5,425,636
[45] Date of Patent: Jun. 20, 1995

[54] ARTICULATOR FOR DENTAL MOLD

[76] Inventor: Duke K. Ghim, 14 Emily Rd., Framingham, Mass. 01701

[21] Appl. No.: 73,647

[22] Filed: Jun. 8, 1993

Related U.S. Application Data

[63] Continuation of Ser. No. 979,971, Nov. 23, 1992, abandoned.

[51] Int. Cl.⁶ .............................................. A61C 11/00
[52] U.S. Cl. .......................................... 433/64; 433/57
[58] Field of Search ...................... 433/57, 60, 61, 62, 433/64

[56] References Cited

U.S. PATENT DOCUMENTS

| | | | |
|---|---|---|---|
| 1,485,657 | 3/1924 | Williams | 433/64 |
| 1,736,006 | 11/1929 | Hagman | 433/64 |
| 1,972,238 | 9/1934 | Reiffel | 425/175 |
| 4,022,419 | 5/1977 | Haker | 249/54 |
| 4,116,416 | 9/1978 | Segura | 249/54 |
| 4,283,173 | 8/1981 | Browne et al. | 249/54 |
| 4,481,162 | 11/1984 | Huffman | 249/54 |
| 4,494,934 | 1/1985 | Huffman | 249/54 |
| 4,533,323 | 8/1985 | Huffman | 433/64 |
| 4,538,987 | 9/1985 | Weissman | 249/54 |
| 4,734,033 | 3/1988 | Huffman | 433/64 |
| 4,767,330 | 8/1988 | Burger | 433/213 |

FOREIGN PATENT DOCUMENTS

| | | | |
|---|---|---|---|
| 3124819 | 2/1982 | Germany | 249/54 |
| 596232 | 12/1947 | United Kingdom | 433/62 |

*Primary Examiner*—John J. Wilson
*Attorney, Agent, or Firm*—John E. Toupal; Harold G. Jarcho

[57] ABSTRACT

An articulator for a dental model including a first link means having first and second ends; a second link means having first and second ends; a hinge connecting the first ends of the first and second links; and a pair of couplings; one connected to the second end of the first link and another connected to the second end of the second link. Each coupling includes a model connector having one end defining a first socket and an opposite end adapted for attachment to a dental model; an articulator connector including a ball portion partially received by the first socket and a stem portion connected to one of the second ends of the links; a second socket partially receiving the ball portion and defining an arcuately shaped aperture penetrated by the stem portion; and a retainer securing the model connector to the second socket.

6 Claims, 4 Drawing Sheets

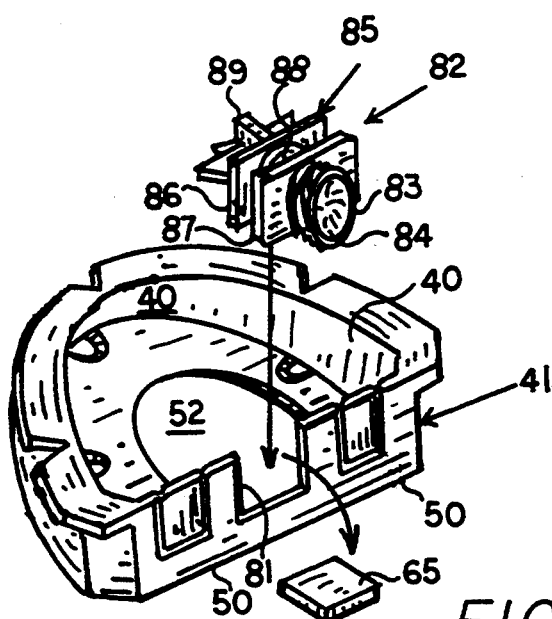
FIG.11
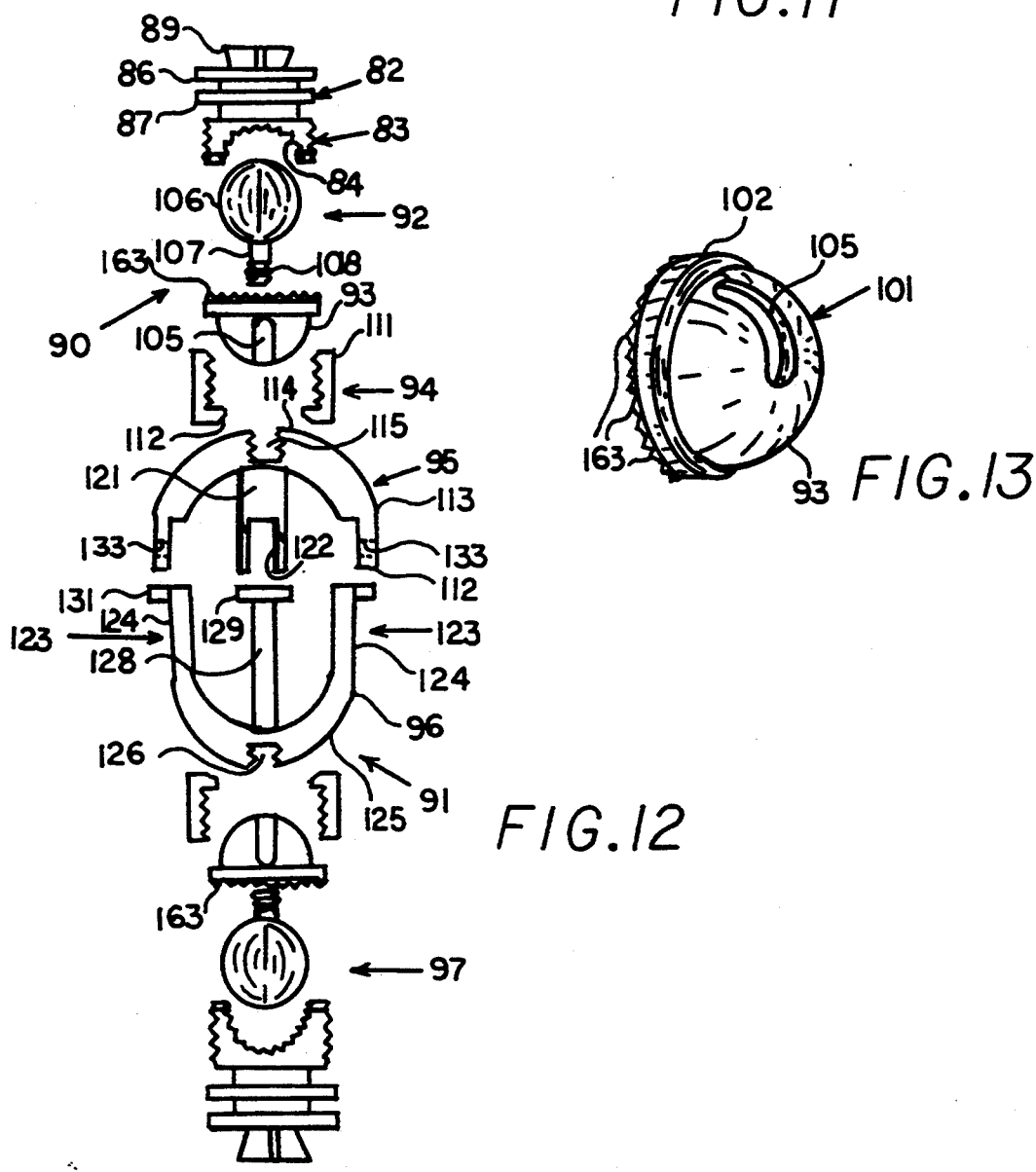
FIG.12
FIG.13

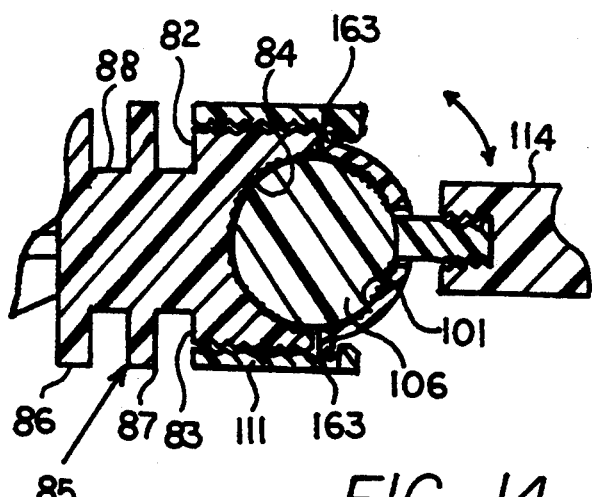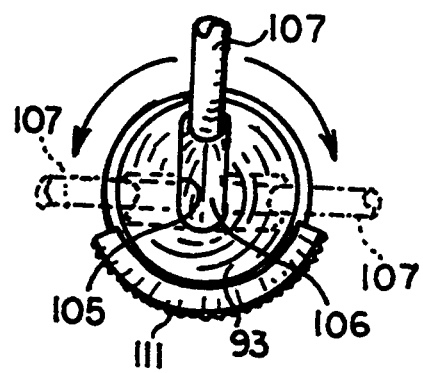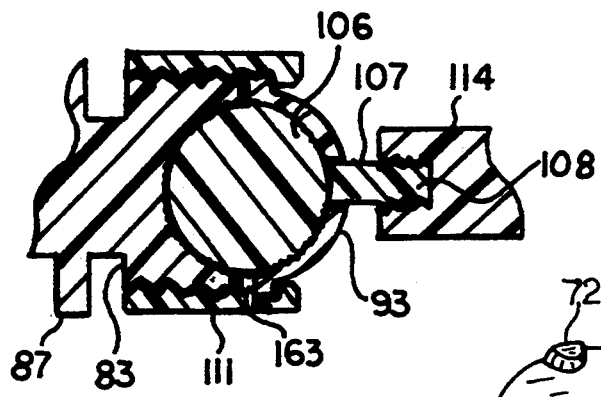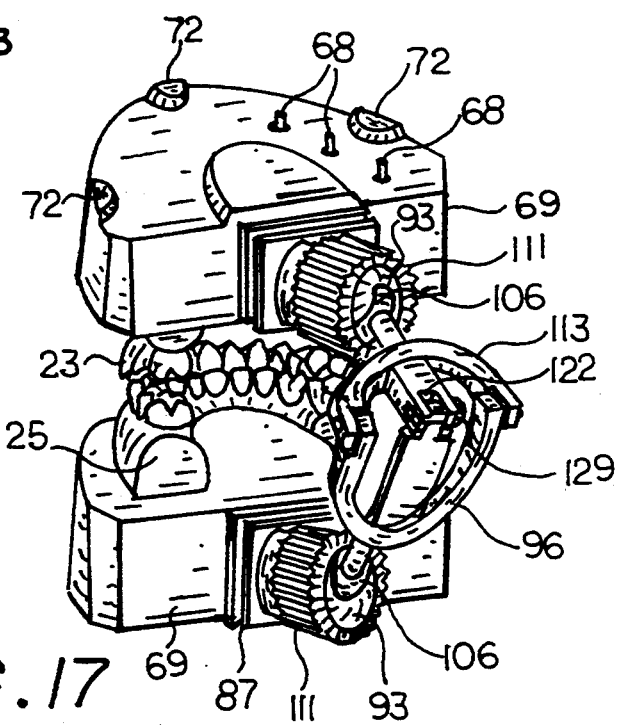

ARTICULATOR FOR DENTAL MOLD

This is a continuation of application Ser. No. 07/979,971 filed on Nov. 23, 1992, now abandoned.

BACKGROUND OF THE INVENTION

This invention relates generally to dental models and, more particularly, to molds and methods for producing bases for dental models and articulators for use therewith. In preparing a prostheses, a dentist normally makes a negative impression of an affected tooth or teeth. The negative impression may be partial, unilateral or bilateral, depending upon the extent of work to be done; and serves as a mold for developing a model of the patient's teeth. Typically, the negative impression is obtained by partially filling a tray with thermoplastic material. The filled tray is inserted within the patient's mouth such that the teeth and adjacent gum sink into and create a cavity within thermoplastic material. Shortly thereafter, the thermoplastic material will cure and retain an exact impression of the patient's teeth and adjacent gum. During the subsequent formation of a tooth die, a pourable casting stone, known as "pink stone" is poured into the negative impression. The pink stone is then compacted to preclude voids and remove any air bubbles and after the pink stone is at least partially cured, wax or similar lubricant is swathed upon the surface of the pink stone.

A base then is combined with the tooth die to complete a dental model. Generally, the base is produced by filling a mold with a pourable, hardenable stone called "yellow stone". Combining of the teeth die and base is accomplished by inserting first portions of pins into the tooth die and then submerging the remaining portions of the pins into the mold before hardening of the yellow stone. Subsequent removal of the mold provides the dental model with the tooth die secured to the base by the embedded pins. An example of this procedure is disclosed in U.S. Pat. No. 4,481,162. By combining a pair of dental models with an articulator element, a full model of a patient's mouth can be simulated.

The object of this invention is to provide an improved mold and articulator for use in producing dental models.

SUMMARY OF THE INVENTION

The invention is a mold for forming the base of a dental model and including a substrate with a continuous periphery formed by a curved section and a substantially straight section, the substrate comprising a soft and easily penetrated receiver portion with a receiver surface defining a first level and recesses defining a second level spaced in a given direction from the first level. Also included are sidewalls extending from the periphery in a direction substantially opposite to the given direction, the substrate and the sidewalls forming a mold cavity for receiving a pourable and hardenable material. The different first and second levels defined by the substrate facilitate the formation of a dental model base that obviates operating procedures previously required.

According to one feature of the invention, the sidewalls slope outwardly from the substrate and the receiver surface and recesses are joined by sloping surfaces. The sloping sidewalls and surfaces simplify removal of the base from the mold.

According to other features, a flange extends transversely from the sidewalls and is joined to edge portions thereof opposite to the substrate periphery and the substrate, the sidewalls, and the flange are an integral unit molded from a soft and easily penetrated plastic material. Integral molding simplifies production of the improved mold.

According to yet other features, the receiver surface comprises a U-shaped surface portion with given outer edge portions intersecting the sidewalls; and the recesses include a central recess having outer edge portions joined to the U-shaped surface and a plurality of spaced apart recesses defined between the sidewalls and outer edge portions of the U-shaped surface. The plural recessed surfaces provide a stable support for the base after combination with a tooth die.

According to still other features, the mold further comprises a plurality of detachable sections defined by the sidewalls. After detachment, the detachable sections create slots that conveniently accommodate a coupling for an articulator.

In another embodiment of the invention, the mold further comprises a detachable divider wall projecting upwardly from the substrate and extending between curved and straight sections of the sidewalls so as to divide the mold cavity into a pair of mold cavities. This embodiment permits the molding of one-half dental models thereby eliminating waste of base material.

The present invention also encompasses a method for forming a dental model and comprising the steps of forming a model die with a gum portion supporting a plurality of teeth and having a plurality of pins, each partially embedded in the gum portion and having an exposed portion extending therefrom opposite to the teeth; forming a mold defining a mold cavity and having a substrate comprising a soft and easily penetrated receiver portion; filling the mold cavity with a pourable and hardenable material; inserting the exposed portions of the pins into said material in the mold cavity; applying force between the substrate and the die so as to produce penetration of the receiver portion of the substrate by substantial lengths of ends of the exposed portions of the pins; allowing the material to harden; and removing from the mold a base formed by the hardened material, retaining the exposed portions of said pins, and from which the ends project. The projecting pin ends can be used to separate discrete tooth sections from the complete dental model.

The invention further encompasses an articulator for a dental model and including an articulator for a dental model and including a first link having first and second ends; a second link having first and second ends; a hinge mechanism connecting the first end of the first link and the first end of the second link; and a pair of couplings; one connected to the second end of the first link and another connected to the second end of the second link; and each coupling including a model connector having one end defining a first socket and an opposite end adapted for attachment to a dental model; an articulator connector including a ball portion partially received by the first socket and a stem portion partially received by the first socket and a stem portion connected to one of the second ends; a second socket partially receiving the ball portion and defining an aperture penetrated by the stem portion; and a retainer securing the model connector to the second socket.

According to features of the articulator, at least one of the ball portions, the first socket, and the second socket is serrated. The serrated surfaces provide a secure connection that eliminate requirements for use of adhesives.

According to another feature, the model connector includes a neck portion and a head portion projecting outwardly from one end of the neck portion, an opposite end of which is connected to said body portion. The neck and head portions facilitate molding of the model connector with a dental model.

According to a further feature, the aperture is arcuate. The arcuate aperture facilitates proper alignment of the articulator.

DESCRIPTION OF THE DRAWINGS

These and other objects and features of the invention will become more apparent upon a perusal of the following description taken in conjunction with the accompanying drawings wherein:

FIG. 11 is an exploded perspective view of a mold and model connector;

FIG. 12 is a disassembled exploded view of an articulator for use with the dental models created with the molds shown in FIGS. 4-10;

FIG. 13 is a perspective view of a component of the articulator shown in FIG. 12;

FIG. 14 is a cross sectional view of a model connector and articulator connector portions of the articulator shown in FIG. 12;

FIG. 15 is an end view of the connector assembly shown in FIG. 14;

FIG. 16 is a cross sectional view of the connector assembly of FIG. 14 shown in a secured position; and FIG. 17 is a perspective view of a dental model formed with the mold shown in FIG. 4 and the articulator shown in FIG. 12.

DESCRIPTION OF THE PREFERRED EMBODIMENT

Figure 1:
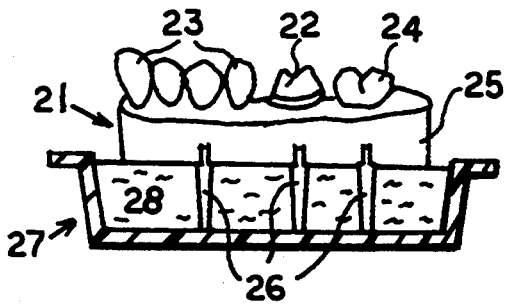
FIG. 1 is a partial cross-sectional view of a dental model and base mold according to the prior art.

FIG. 1 illustrates a dental model being formed in accordance with the prior art. Typically, a dentist when preparing a dental prostheses makes an impression of a patient's mouth in a negative form. The negative form then is used to create with a suitable gypsum material a tooth die 21 including, for example, a prepared tooth 22, adjacent teeth 23 and 24 and a gum portion 25. Next, tapered dowel pins 26 are inserted into the gum portion 25 in alignment with the teeth 22-24. Finally, the die 21 is inserted into a mold 27 filled with a pourable and hardenable material 28 such as yellow stone until the bottoms of the dowel pins 26 rest upon the bottom of the mold 27 as shown in FIG. 1.

Figure 2:
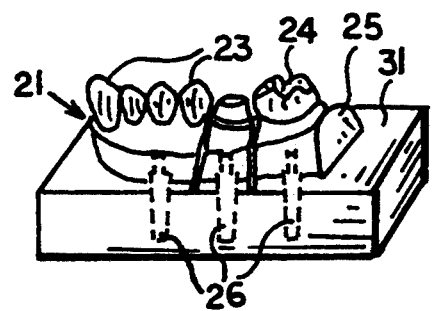
FIG. 2 is a perspective view of the dental model of FIG. 1 after molding of a base therefor.
Figure 3:
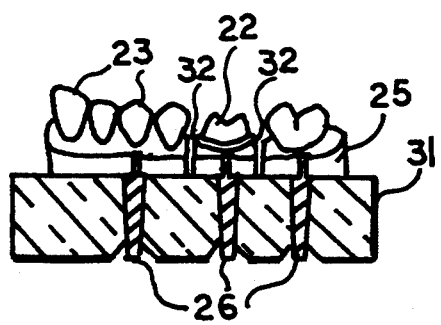
FIG. 3 is a partial cross-sectional view of the dental model shown in FIG. 2.

After removal of the mold 27, the cured yellow stone 28 provides a base 31 secured to the die 21 by the jointly retained dowel pins 26 as shown in FIGS. 2 and 3. The subsequent creation of a prostheses such as a crown for the prepared tooth 22 is facilitated by separation thereof from the complete model 21. To accomplish this separation, a thin saw is used to create cuts 32 between the prepared tooth portion 22 and the adjacent tooth portions 23, 24. The prepared tooth 22 then can be removed by withdrawing its dowel pin 26 from the model base 31. However, because of the adherence typically exhibited between the dowel pins 26 and the model base 31, an easy removal of any of the tooth models 22-24 requires removal by, for example, cutting or chipping of the base material to expose the ends of the dowel pins 26 as shown in FIG. 3. The exposed ends of the dowel pins 26 then can be pressed to force pins out of the base 31 and allow separation of the individual tooth portions 22-24. The exposure of the ends of the dowel pins 26, generally with a knife or drill, is undesirably time consuming, dust producing and personal injury prone.

Figure 4:
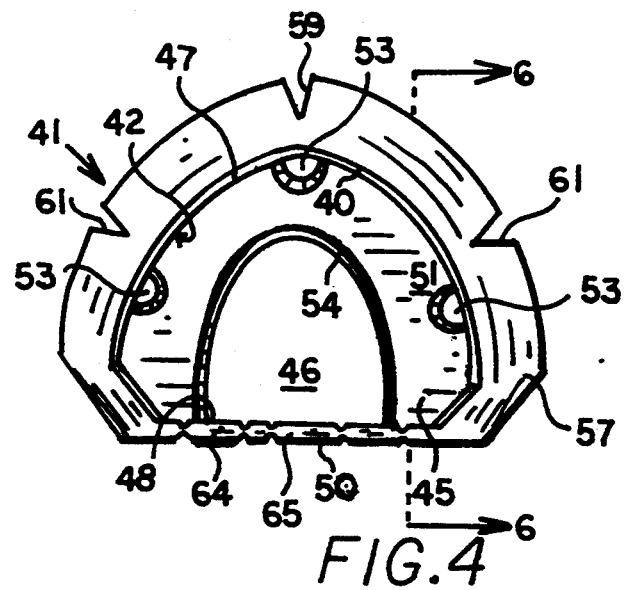
FIG. 4 is a top view of a mold for a dental model in accordance with the present invention.
Figure 5:
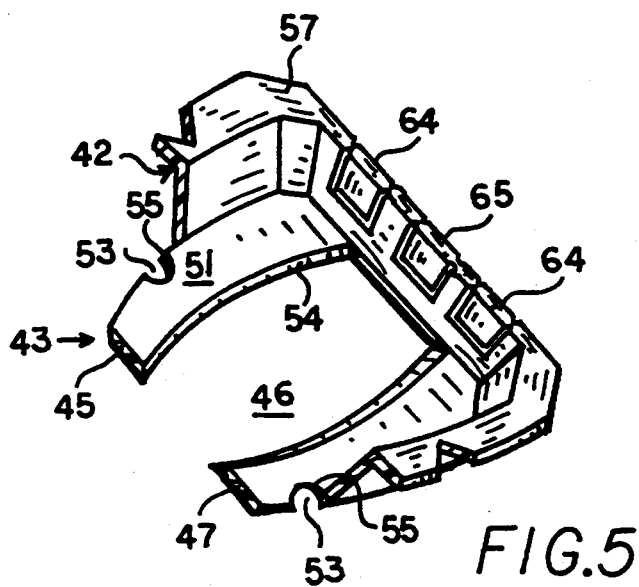
FIG. 5 is a partially cut away perspective view of the mold shown in FIG. 4.

Referring now to FIGS. 4 and 5, there is shown in accordance with the present invention, an improved mold 41 for forming the base of a dental model. The mold 41 includes sidewall portions 42 extending from a substrate 43 to form a cavity 44. Forming the substrate 43 is a U-shaped thick receiver portion 45 partially encompassing a central opening 46. As shown, the sidewalls 42 include a curved wall portion 40 and a straight wall portion 50 that extend upwardly and slope outwardly from, respectively, outer peripheries of the receiver portion 45 and the central opening 46. The receiver portion 45 provides a U-shaped receiver surface 51 defining a first level of the substrate 43 above a second level defined by its bottom surface 47 and spaced from the receiver surface 51 in a direction opposite to the projected sidewalls 42. Also formed in the substrate 43 and intersecting the sidewalls 42 are a plurality of apertures 53 spaced apart and separated from each other on the receiver surface 51. The opening 46 and apertures 53 are defined, respectively, by sloping side surfaces 54, 55 of the receiver portion 45. Extending outwardly from upper edges of the curved sidewall 40 opposite to the substrate 43 is a transverse flange 57. Formed in the flange 57 are a triangular notch 59 aligned with the mid-point of the curved wall portion 40 and a triangular notch 61 in each opposite portion of the flange 57 extending between the triangular notch 59 and the straight wall portion 50. Also formed in the straight wall portion 50 are a central tab 65 and straddling spaced apart side tabs 64. Preferably, the substrate 43, the sidewalls 42, and the flange 57 are an integral unit molded from a soft and easily penetrated plastic material such as polystylene.

Figure 6:
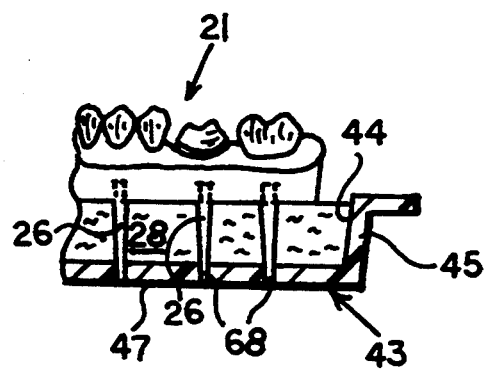
FIG. 6 is a partial cross-sectional view of a dental model and the mold shown in FIGS. 4 and 5.
Figure 7:
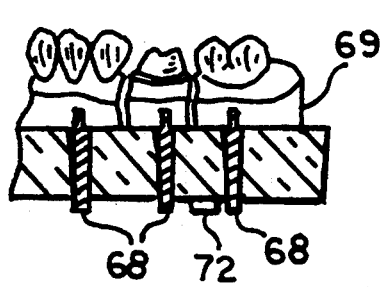
FIG. 7 is a partial cross sectional view of the dental model of FIG. 6 after formation of a base with the mold shown in FIGS. 4 and 5.
Figure 8:
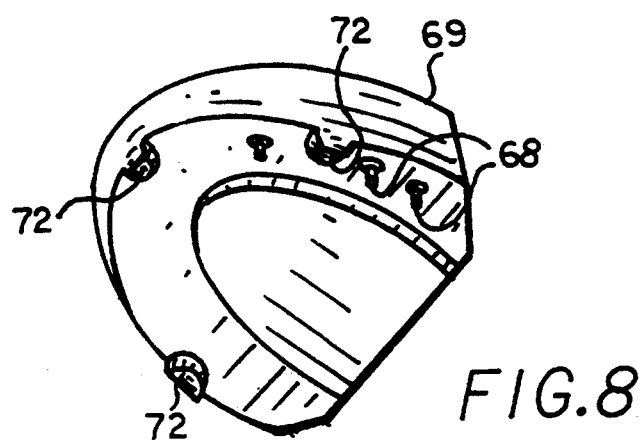
FIG. 8 is a bottom perspective view of the dental model shown in FIG. 7.

The mold 41 is used in a similar manner to that described above in conjunction with the mold 27 of FIG. 1. However, prior to use of the mold 41 the central tab 65 in the straight wall portion 50 is removed to create a slot 81 as shown in FIG. 11. Next, a model connector 82 is engaged with the mold 41. The model connector 82 includes an externally threaded body portion 83 that defines a first serrated socket 84 and a head portion 85 joined to the body portion 83. Included in the head portion 85 are spaced apart flanges 86, 87 joined by a neck portion 88. An anchor portion 89 extends from the flange 86 in a direction opposite to the body portion 83. The model connector 82 is engaged with the mold 41 by insertion of the neck portion 88 of the head portion 85 into the slot 81 created by removal of the central tab 65 and with the flanges 86, 87 engaging opposite surfaces of the straight wall portion 50. Next, with the bottom surface 47 of the substrate 43 resting on a, preferably, wax paper covered surface such as a table, the tooth die 21 is inserted into the mold cavity 44 which has been filled with pourable and hardenable yellow stone 28, and a force is applied between the substrate 43 and the die 21 causing substantial lengths 68 of the exposed portions of the pins 26 to penetrate the receiver portion 45 as shown in FIG. 6. After hardening of the yellow stone 28 and removal of the mold 41, the still exposed lengths 68 of the pins 26 project out of a molded base 69 so as to be readily accessible to the application of force when a given segment of the model 21 is to be removed. Also the anchor portion 89 of the mold connector 82 is securely retained within the hardened base 69. Thus, the present invention eliminates the above noted procedure for removing a portion of the base 69 to expose outer portions of the pins 26. In addition, removal of the base 69 from the mold 41 is simplified by the notches 58, 59 and 61 in the flange 57, the outwardly sloping sidewalls 42 and the sloping surfaces 54, 55 between the receiver surface 51 and, respectively, the opening 52 and the apertures 53.

A central leg 71 and spaced apart peripheral legs 72 formed on the base 68, by, respectively, the central opening 52 and the apertures 53 of the substrate 43 provide stable support for the model 21 when placed on a work surface and prevent the application force thereby on the exposed ends 68 of the pins. Thus inadvertent dislodgement of portions of the model 21 from the base 69 is prevented.

Figure 9:
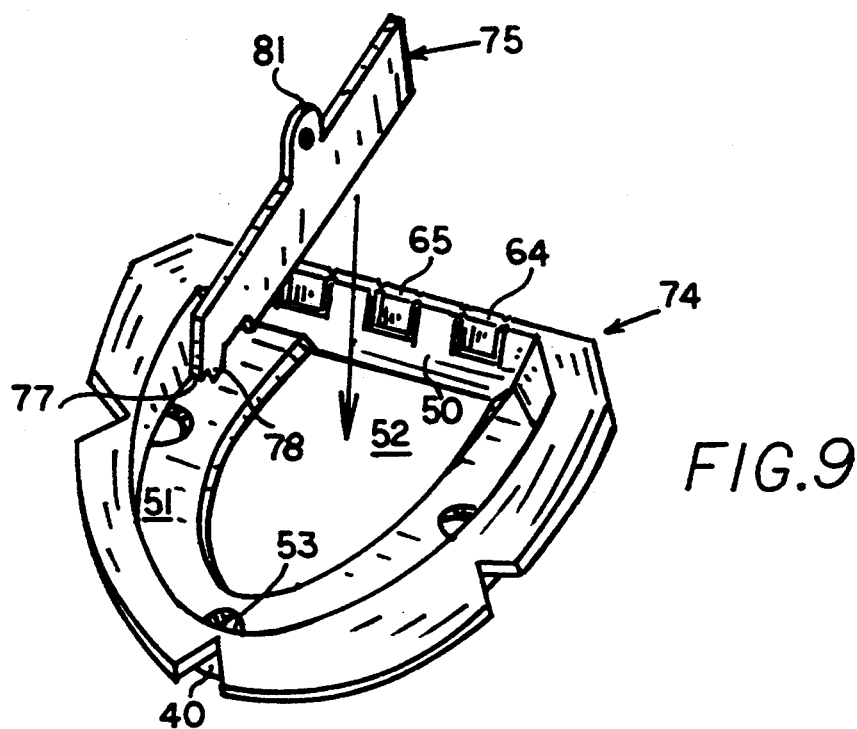
FIG. 9 is a disassembled perspective view of another mold embodiment for forming a base for a dental model.
Figure 10:
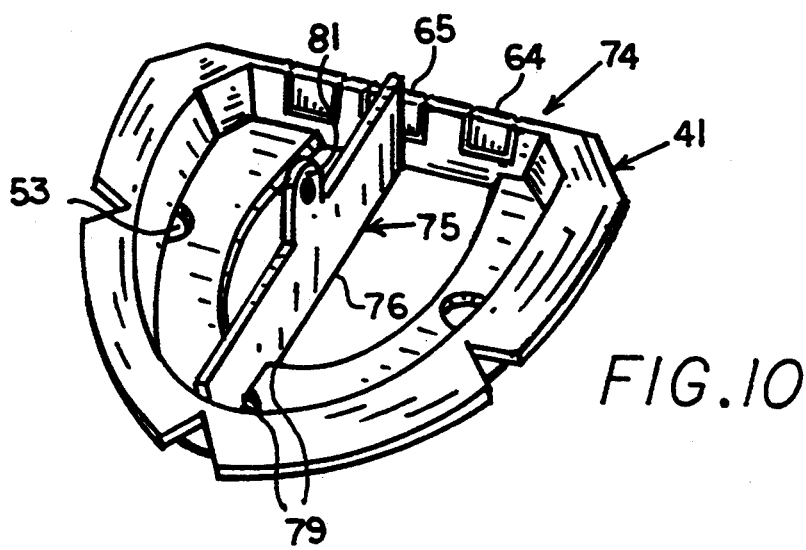
FIG. 10 is an assembled perspective view of the mold shown in FIG. 9.

Another mold embodiment 74 of the invention is illustrated in FIGS. 9 and 10. In addition to the mold 41 shown in FIGS. 4 and 5, the mold embodiment 74 includes a divider wall 75. Forming a bottom edge of the divider wall 75 is an elongated portion 76 with a length equal to the longitudinal length of the central opening 52, a shorter elevated portion 77 and a tab 78 for entering a centrally located aperture. Extending from an upper edge of the divider wall 75 is an apertured projection handle 81.

The embodiment 74 is used in those cases in which only one-half a dental model is required. In those cases, the divider wall 75 is positioned in a mold 41 as shown in FIG. 10. When properly positioned, one end of the divider wall 74 engages a mid-point of the straight sidewall 50 and the opposite end engages the mid-point of the curved sidewall 40. In addition, the elongated bottom edge portion 76 is received by the opening 52, the shorter portion 77 engages the receiver surface 51 and the tab 78 is received by the middle aperture 53 so as to divide the mold 41 into equal halves. Either half of the mold embodiment 74 can be used to prepare a one-half dental model in the manner described above in connection with the use of the mold 41 shown in FIGS. 4 and 5.

Illustrated in FIG. 13 is an articulator 91 for use with dental models produced by either the mold embodiment 41 of FIG. 4 or the mold embodiment 74 of FIGS. 9 and 10. The articulator 91 includes a first coupling 90 having the model connector 82 (FIG. 11), an articulator connector 92, a semi-spherical member 93, and a retainer 94; a first link 95, a second link 96 and a second coupling 97 identical to the first coupling 90. As shown in FIGS. 13 and 14, the semi-spherical member 93 defines a serrated second socket 101 terminated by an outwardly projecting circular shoulder portion 102 having a serrated outer surface 103. Formed in the semi-spherical member 93 and intersecting the second socket 101 is an arcuately shaped aperture 105.

The articulator connector 92 includes a serrated ball portion 106 and an integrally formed stem portion 107 having a threaded outer end 108. Forming the retainer 94 is an internally threaded cylindrical portion 111 having at one end an inwardly directed flange portion 112. The first link 95 is U-shaped and includes a first end 112 formed by terminations of bifurcations 113 and a second end 114 defined by a yoke having an internally threaded hole 115. Also included in the first link 95 is a shaft 121 having extending from the second end 114 between the bifurcations 113 and defining a slot 122. Similarly, the second link 96 has a first end 123 formed by terminations of bifurcations 124 and a second end 125 defined by a yoke having an internally threaded hole 126. Extending from the second end 125 between the bifurcations 124 is a pin 128 with a head 129 for engagement in the slot 122 of the first link 95. Outwardly projecting shafts 131 on the bifurcations 124 are arranged for reception by apertures 133 formed in the bifurcations 113 so as to provide a hinged connection between the first link 95 and the second link 96. Insertion of the shafts 131 into the openings 133 is accomplisehd by first compressing the bifurcations 124, positioning the compressed bifurcations 124 between the bifurcations 113 and then removing force from the bifurcations 124 allowing the shafts 131 to enter the openings 133 in the first link 195.

During assembly of the first coupling 90, the ball portion 106 of the articulator 92 is inserted into the first socket 84 of the mold connector 82, the anchor portion 89 of which has been molded into a dental model created by a mold 41. Next, the semi-spherical member 93 is positioned over the ball portion 106 of the articulator connector 92 with the stem portion 107 projecting through the arcuate aperture 105 as shown in FIG. 14. The retainer 94 then is turned onto the externally threaded body 83 of the model connector 82 to retain the ball portion 106 of the articulator connector 92 within the first socket 84 and the second socket 101. Connection of the first coupling 90 to the first link 95 is accomplished by turning the threaded outer end 108 of the stem portion 107 into the internally threaded hole 115 in the second end 114 of the first link 95. The second coupling 97 is attached in a similar manner between the second end 125 of the second link 196 and another dental model created by a mold 41. After establishing a pivotable hinged connection between the first and second links 95, 96, as described above, a full dental model is created as illustrated in FIG. 17.

With the first and second couplings 90, 97 loosely engaged as shown in FIG. 14, the dental models are arranged to provide desired relative up and down and side to side chewing motion in the following manner. A desired arrangement of the stem portions 107 of the articulator connectors 92 in one sense is established by rotating the spherical member 93 to accommodate a desired orientation in one sense as shown by dashed lines in FIG. 15 and each stem portion 107 is then pivoted in its associated arcuate aperture 105 of the spherical member 93 to create a desired orientation in another sense as shown by dashed lines in FIG. 14. After establishment of the desired orientations for the stem portions 107 of the articulator connectors 92, the retainers 94 are tightened on the body portions 83 of the model connectors 82 creating a highly secure engagement between the serrated ball portions 106 of the articulator connectors 92 and the first sockets 84 of the model connectors 82 and the second sockets 101 of the spherical members 93. Additional immobility within the coupling 90 is established by forcible engagement between the serrated surface 103 on the shoulder portions 102 of the spherical members 93 and the body portions 83 of the model connectors 82.

The articulator 91 is used in a similar manner to provide a dental model with one-half bases formed with the mold embodiment 74 shown in FIGS. 9 and 10. In this case however, each of the model connectors 82 is secured within a selected slot produced by detachment of one of the straddling tabs 64 shown in FIG. 9. Otherwise the assembly and use of a one-half model is the same as described above in connection with the full model of FIG. 17.

Obviously, many modifications and variations of the present invention are possible in light of the above teachings. It is to be understood, therefore, that the invention can be practiced otherwise than as specifically described.

What is claimed:

1. An articulator for a dental model and comprising:
a first link means having first and second ends;
a second link means having first and second ends;
hinge means connecting said first end of said first link means and said first end of said second link means; and
a pair of coupling means; one connected to said second end of said first link means and another connected to said second end of said second link means; and each said coupling means comprising a model connector means having one end defining a first socket and an opposite end adapted for attachment to a dental model; an articulator connector including a ball portion partially received by said first socket and a stem portion connected to one of said second ends of said link means; a second socket partially receiving said ball portion and defining an arcuately shaped aperture penetrated by said stem portion; and a retainer securing said model connector to said second socket.

2. An articulator according to claim 1 wherein at least one of said ball portion, said first socket, and said second socket is serrated.

3. An articulator according to claim 2 wherein each of said ball portion, said first socket and said second socket is serrated.

4. An articulator according to claim 1 wherein said model connector means includes an externally threaded body portion, said second socket includes an outwardly projecting shoulder portion, and said retainer includes an internally threaded cylindrical portion engaging said body portion and an inwardly projecting flange portion engaging said shoulder portion.

5. An articulator according to claim 4 wherein said model connector means includes a neck portion and a head portion projecting outwardly from one end of said neck portion, an opposite end of which is connected to said body portion.

6. An articulator according to claim 1 wherein said first link is U-shaped and has a first pair of leg portions joined by a first connector portion, each of said first leg portions having an end with a first hinge portion of said hinge means and said first hinge portions being spaced apart a given distance; and said second link is U-shaped and has a second pair of leg portions joined by a second connector portion, each of said second leg portions having an end with a second hinge portion of said hinge means and said second hinge portions being spaced apart said given distance and engaged with said first hinge portion so as to provide therewith a pair of pivotable connections between said first and second links, and wherein said pivotable connections are adapted for disengagement in response to a flexing of either of said first or second links to substantially change therefor said given distance.

* * * * *